(12) United States Patent
Feng et al.

(10) Patent No.: US 6,265,750 B1
(45) Date of Patent: Jul. 24, 2001

(54) ELECTROCHEMICAL GAS SENSOR AND METHOD OF MAKING THE SAME

(75) Inventors: Chang-Dong Feng, Long Beach; Edmond Y. Chu, San Diego, both of CA (US)

(73) Assignee: Teledyne Technologies Incorporated, Los Angeles, CA (US)

( * ) Notice: Subject to any disclaimer, the term of this patent is extended or adjusted under 35 U.S.C. 154(b) by 0 days.

(21) Appl. No.: 09/353,907

(22) Filed: Jul. 15, 1999

(51) Int. Cl.[7] .................................................. H01L 27/14
(52) U.S. Cl. ........................................... 257/414; 257/428
(58) Field of Search ..................... 438/49, 56; 257/428, 257/414; 73/31.05, 31.06; 422/98; 435/807; 204/415, 424, 426, 431, 432

(56) References Cited

U.S. PATENT DOCUMENTS

| | | | |
|---|---|---|---|
| 4,668,374 | * 5/1987 | Bhagat et al. | 204/425 |
| 4,874,500 | * 10/1989 | Madau et al. | 204/412 |
| 5,102,525 | * 4/1992 | Miyahara et al. | 204/415 |
| 5,183,549 | * 2/1993 | Joseph et al. | 204/415 |
| 5,310,610 | * 5/1994 | Furubayashi et al. | 430/11 |
| 5,788,832 | 8/1998 | Howard et al. | 205/775 |
| 5,837,454 | 11/1998 | Cozzette et al. | 435/6 |
| 5,883,009 | 3/1999 | Villa et al. | 438/739 |

FOREIGN PATENT DOCUMENTS

2267348 * 1/1993 (GB) .

* cited by examiner

Primary Examiner—Carl Whitehead, Jr.
Assistant Examiner—Jeff Vockrodt
(74) Attorney, Agent, or Firm—Kirkpatrick & Lockhart LLP

(57) ABSTRACT

An electrochemical gas sensor including a substrate defining an opening therethrough, a sensing electrode connected to a first surface of the substrate and adjacent a first end of the opening, a diffusion barrier connected to the sensing electrode, a counter electrode adjacent a second end of the opening, and an electrolyte located in the opening between the sensing electrode and the counter electrode.

31 Claims, 6 Drawing Sheets

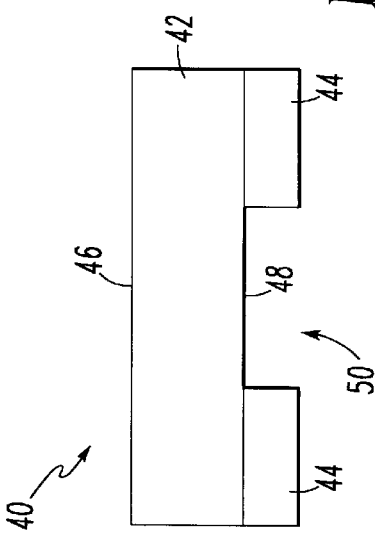
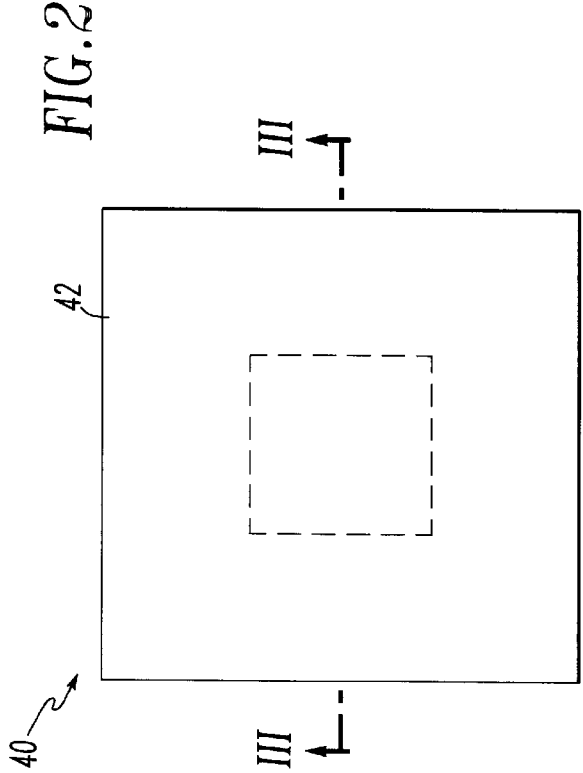
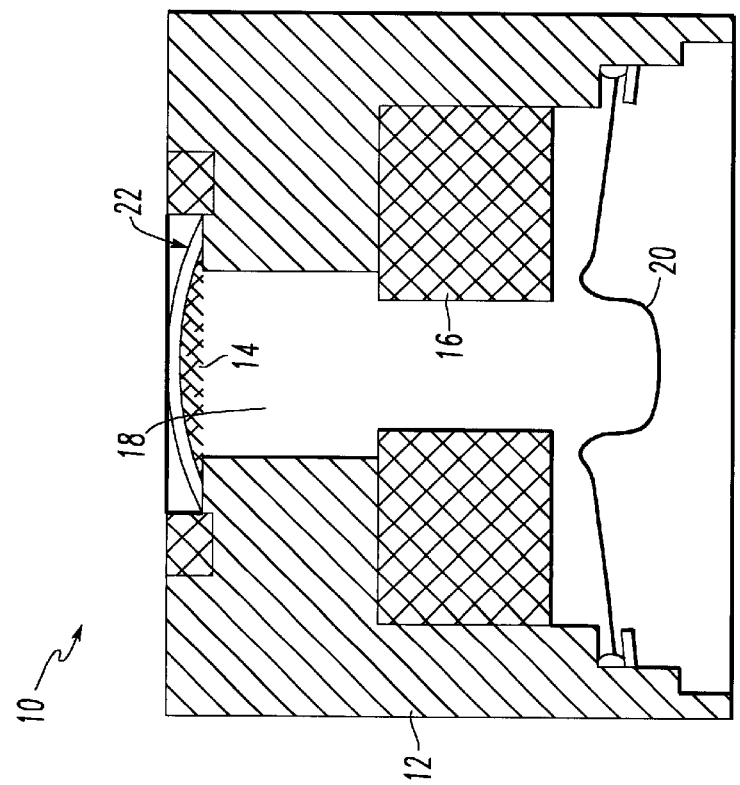

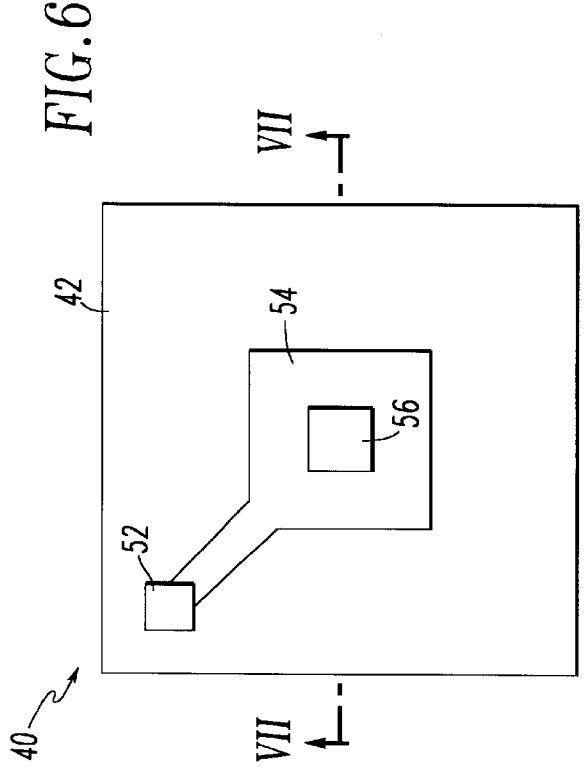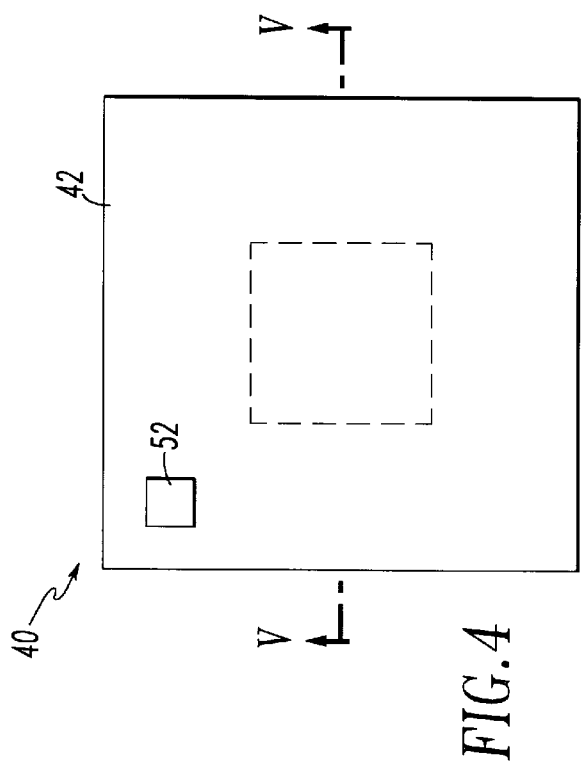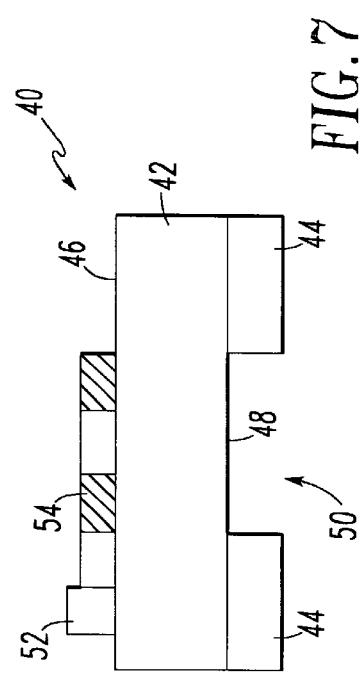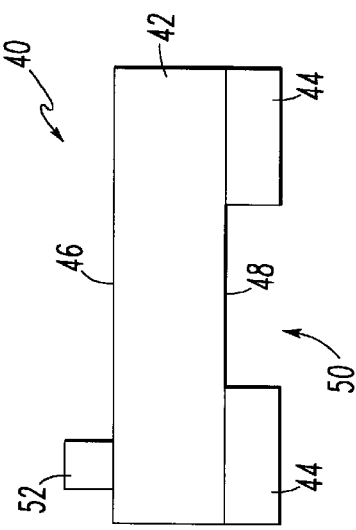

ELECTROCHEMICAL GAS SENSOR AND METHOD OF MAKING THE SAME

CROSS-REFERENCE TO RELATED APPLICATIONS

Not Applicable.

STATEMENT REGARDING FEDERALLY SPONSORED RESEARCH AND DEVELOPMENT

Not Applicable.

BACKGROUND OF THE INVENTION

1. Field of the Invention

The present invention is directed generally to an electrochemical gas sensor, and more particularly to an electrochemical gas sensor in which a portion of the components are formed using microelectromechanical systems technology.

2. Background of the Invention

Electrochemical gas sensors are typically employed in monitoring equipment, such as in equipment used in medical applications, to measure the concentration of a particular gas in a gas sample. Such equipment typically includes a display to indicate numerical readings of gas concentrations and typically provides output waveforms corresponding to the gas concentrations.

FIG. 1 illustrates a typical electrochemical gas sensor 10 of the relevant art. The sensor 10 includes a housing 12 which contains the components of the sensor 10. A sensing electrode 14 may be constructed of, for example, a noble metal such as silver. A counter electrode 16 may be constructed of, for example, lead. An electrolyte 18 such as, for example, an aqueous solution of potassium hydroxide, fills the housing 12. Together, the sensing electrode 14, counter electrode 16, and electrolyte 18 form an electrochemical cell. An expansion membrane 20 allows for expansion and contraction of the electrolyte 18 without damaging the sensor 10. A diffusion barrier 22, such as a membrane made of fluoropolymer resin sold under the trade name Teflon®, a registered trademark of E.I. Du Pont de Nemours and Company, is adjacent the sensing electrode 14, and limits the diffusion rate of the gas to be measured by the sensor 10.

Typical relevant art sensors 10 are manufactured serially. That is, the sensors 10 are manufactured from different and discrete components according to many assembly and sealing processing steps. Thus, there is little cost benefit in manufacturing sensors 10 in high volume quantities. In addition, conventional sensors are often relatively large, about ten cubic centimeters, making them too intrusive for many applications.

The performance of relevant art sensors 10 is also limited by the characteristics of the discrete components of the sensor 10, as well as the required assembly process. The diffusion barrier 22 of the sensor 10 limits the capability of the sensor 10 to monitor rapid changes in gas concentrations: the thicker the diffusion barrier 22, the slower the response time of the sensor 10. Typical relevant art sensors 10 have a diffusion barrier 22 of at least five to six microns. A typical response time for such a relevant art sensor 10 is approximately 500 ms. Such response times may not be acceptable for many applications. Moreover, the minimum thickness of the diffusion barrier 22 is limited to the availability of materials from commercial suppliers and the handling requirements during conventional sensor assembly. Thus, the response times of relevant art electrochemical gas sensors are limited to values which may not be fast enough for some applications.

In addition, typical relevant art sensors 10 are temperature and pressure dependent, and do not allow for integration of electrical systems to compensate for the effects of temperature and pressure.

Accordingly, there exists a need in the relevant art for an electrochemical gas sensor which is less expensive to produce and which is smaller in size. There also exists a need for an electrochemical gas sensor which realizes faster response times than relevant art sensors in response to rapid changes in the concentration of the gas to be measured. There also exists a need for an electrochemical gas sensor which allows for the integration of other sensing elements and electronic circuits.

BRIEF SUMMARY OF THE INVENTION

The present invention is directed to an electrochemical gas sensor. The electrochemical gas sensor includes a substrate defining an opening therethrough, a sensing electrode connected to a first surface of the substrate and adjacent a first end of the opening, a diffusion barrier connected to the sensing electrode, a counter electrode adjacent a second end of the opening, and an electrolyte located in the opening between the sensing electrode and the counter electrode.

The present invention represents a substantial advance over relevant art electrochemical gas sensors. The present invention has the advantage that it can be manufactured at a lower cost of production in comparison to relevant art gas sensors. The present invention also has the advantage that the size of the sensor is significantly reduced in comparison to relevant art sensors. The present invention has the further advantage that it has a fast response time in response to changes in the concentration of input gas. The present invention also has the advantage that it allows for the integration of compensating electronics and other electrical circuits. These and other advantages and benefits of the present invention will become apparent from the Detailed Description of the Invention hereinbelow.

BRIEF DESCRIPTION OF THE DRAWINGS

For the present invention to be clearly understood and readily practiced, the present invention will be described in conjunction with the following figures, wherein:

FIG. 1 is a cross-sectional view of a typical electrochemical gas sensor of the relevant art;

FIG. 2 is a top plan view of a substrate assembly of an electrochemical gas sensor according to the present invention after formation of an etching mask;

FIG. 3 is a cross-sectional side-view of the substrate assembly of FIG. 2;

FIG. 4 is a top plan view of the substrate assembly of FIG. 2 after formation of a contact pad;

FIG. 5 is a cross-sectional side-view of the substrate assembly of FIG. 4;

FIG. 6 is a top plan view of the substrate assembly of FIG. 4 after formation of a sensing electrode lead;

FIG. 7 is a cross-sectional side-view of the substrate assembly of FIG. 6;

DETAILED DESCRIPTION OF THE INVENTION

Figure 10:
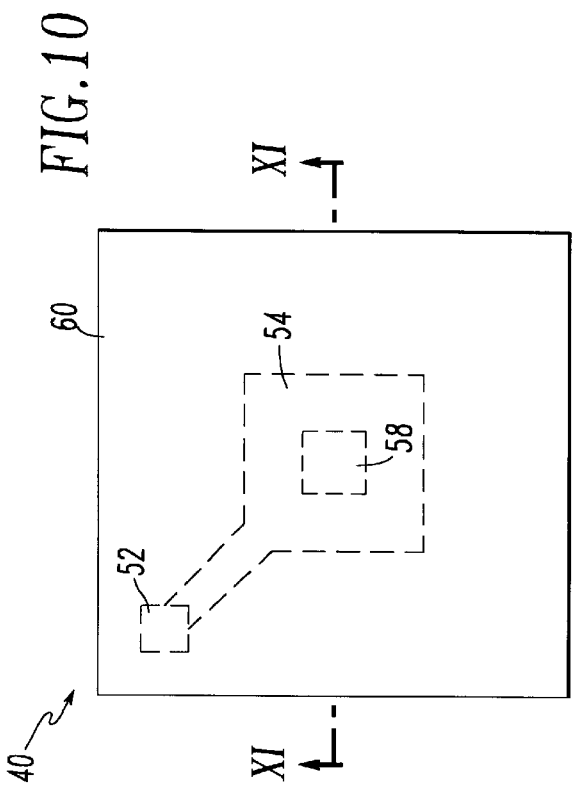
FIG. 10 is top plan view of the substrate assembly of FIG. 8 after formation of a diffusion barrier.

FIGS. 2–16 illustrate various stages in the progression of forming an electrochemical gas sensor on a substrate assembly 40 according to the present invention. The substrate assembly 40 includes a substrate 42 and a portion of the components of the electrochemical gas sensor. The substrate 42 is the lowest layer of material on a wafer, such as for example, a single crystal silicon wafer. A portion of the components of the electrochemical gas sensor may be formed on the substrate 42 using, for example, microfabrication processes.

Microfabrication, also known as micromachining, commonly refers to the use of known semiconductor processing techniques to fabricate devices known as microelectromechanical systems (MEMS) devices. In general, known MEMS fabrication processes involve the sequential addition and removal of layers of material from a substrate layer through use of film deposition and etching techniques until the desired structure has been realized. Accordingly, MEMS devices typically function under the same principles as their macroscale counterparts. MEMS devices, however, offer advantages in design, performance, and cost in comparison to their macroscale counterparts due to the decrease in scale of MEMS devices. In addition, due to batch fabrication techniques applicable to MEMS technology, significant reductions in per unit cost may be realized.

As noted hereinbefore, MEMS fabrication techniques have been largely derived from the semiconductor industry. Accordingly, such techniques allow for the formation of structures on a substrate using adaptations of patterning, deposition, etching, and other processes that were originally developed for semiconductor fabrication. In general, these processes start with a substrate, such as a wafer of silicon. Multiple devices are then fabricated from the wafer through sequential addition and removal of layers of material. For example, various film deposition technologies, such as vacuum deposition, spin coating, dip coating, and screen printing may be used for thin film and thick film deposition of layers on the substrate. Layers of thin film may be removed, for example, by wet or dry surface etching, and parts of the substrate may be removed by, for example, wet or dry bulk etching. Once the fabrication of the devices on the substrate is complete, the wafer is sectioned, or diced, to form multiple individual MEMS devices. The individual devices are then packaged to provide for electrical connection of the devices into larger systems and components. The processes used for external packaging of the MEMS devices are generally analogous to those used in semiconductor manufacturing.

MEMS devices have the desirable feature that multiple MEMS devices may be produced simultaneously in a single batch by processing many individual components on a single wafer. For example, numerous individual electrochemical gas sensors may be formed on a single silicon substrate. Accordingly, the ability to produce numerous electrochemical gas sensors in a single batch results in a cost saving in comparison to the serial nature in which relevant art electrochemical gas sensors are manufactured.

In addition to decreasing per unit cost, MEMS fabrication techniques also reduce the relative size of MEMS devices in comparison to their macroscale counterparts. Therefore, an electrochemical gas sensor manufactured according to MEMS fabrication techniques allows for smaller electrochemical gas sensors, which in turn provides faster response times because of the decreased thickness of the diffusion layer. An electrochemical gas sensor according to the present invention may be used, for example, in medical applications, such as in a ventilator to monitor the in situ oxygen level of a patient.

FIGS. 2 and 3 illustrate a top plan view and a cross-sectional side view, respectively, of an electrochemical gas sensor having the substrate assembly 40 according to the present invention at an early stage in the fabrication thereof. The substrate assembly 40 includes the substrate 42 and a portion of the components of the electrochemical gas sensor. As described hereinbelow, the portion of the components of the gas sensor are formed directly on the substrate 42 as various additional layers or structures, although, in other embodiments, the components may be formed on one or more intervening layers. The substrate assembly 40 illustrated in FIGS. 2 and 3 further includes an etching mask 44. The substrate 42 is a non-conducting material such as, for example, a single crystal silicon wafer. The substrate 42 has a first surface 46 and a second surface 48. The etching mask 44 is formed on the second surface 48 of the substrate 42, and may be any material resistant to bulk etching of the substrate 42 such as, for example, silicon nitride. For an embodiment where the etching mask 44 is silicon nitride, the mask 44 may be formed on the substrate 42 by, for example, chemical vapor deposition. After the etching mask 44 is formed, it is patterned, such as by a conventional surface etch, to form a bulk etching area 50.

FIGS. 4 and 5 illustrate the substrate assembly 40 with a contact pad 52 formed on the first surface 46 of the substrate 42. The contact pad 52 provides a surface for external connection of the sensor after final assembly, as described hereinbelow. The contact pad 52 is an electrically conductive material such as, for example, gold or aluminum, and may be formed by conventional thin film deposition techniques, such as vacuum deposition or screen printing. The contact pad 52 may be patterned to the desired shape and orientation using, for example, conventional surface etching techniques.

FIGS. 6 and 7 illustrate the substrate assembly 40 with a sensing electrode lead 54 formed on the first surface 46 of the substrate 42. The sensing electrode lead 54 is an electrically conductive material such as, for example, a noble metal such as silver, gold, platinum, or rhodium, and may be formed using conventional film deposition and surface etching techniques. The sensing electrode lead 54 is in electrical contact with the contact pad 52, and may also define an opening 56 for a sensing electrode 58, as described hereinbelow with reference to FIGS. 8 and 9.

Figure 8:
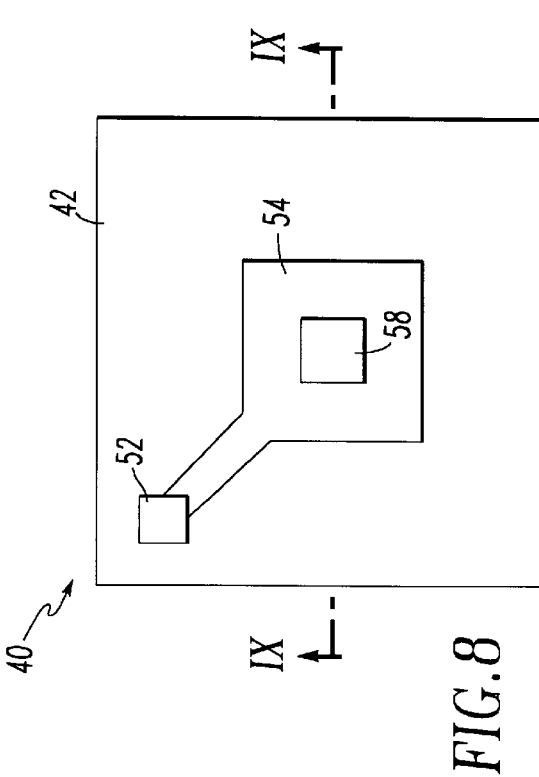
FIG. 8 is a top plan view of the substrate assembly of FIG. 6 after formation of a sensing electrode.
Figure 9:
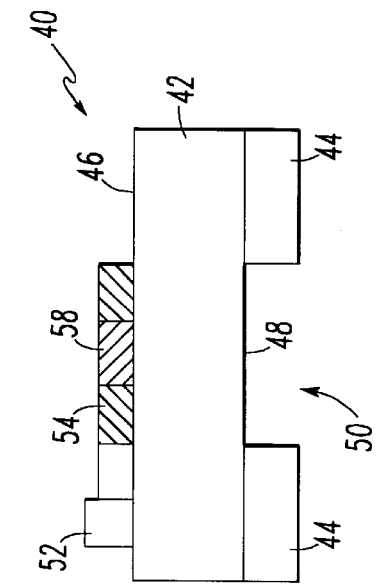
FIG. 9 is a cross-sectional side-view of the substrate assembly of FIG. 8.

FIGS. 8 and 9 illustrate the substrate assembly 40 with the sensing electrode 58 formed on the first surface 46 of the substrate 42. The sensing electrode 58 is an electrically conductive material such as, for example, a noble metal, such as gold, silver, platinum, or rhodium. The sensing electrode 58 is in electrical contact with the sensing electrode lead 54, such as according to the embodiment illustrated in FIGS. 8 and 9, in which the sensing electrode 58 is formed within the opening 56 defined by the sensing electrode lead 54. The sensing electrode 58 may be formed according to conventional film deposition and patterning techniques.

Figure 11:
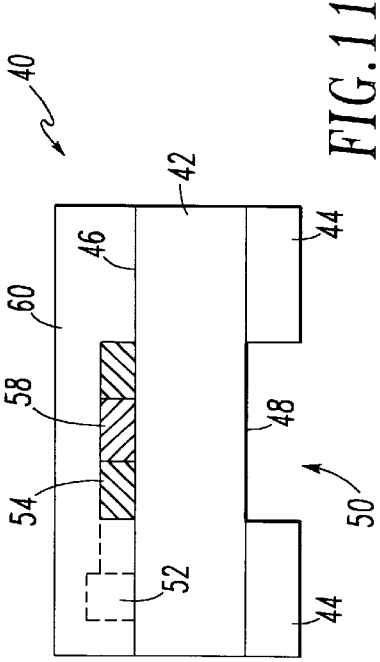
FIG. 11 is a cross-sectional side-view of the substrate assembly of FIG. 10.

FIGS. 10 and 11 illustrate the substrate assembly 40 with a diffusion barrier 60 formed on the first surface 46 of the substrate 42 before patterning of the diffusion barrier 60. The diffusion barrier 60 may be a hydrophobic material such as, for example, Teflon® fluoropolymer resin. The diffusion barrier 60, before patterning, is in contact with the contact pad 52, the sensing electrode lead 54, the sensing electrode 58, and the substrate 42. The diffusion barrier 60 may be deposited by conventional thin film deposition techniques, allowing the thickness of the diffusion barrier to be as small as one micron.

Figure 12:
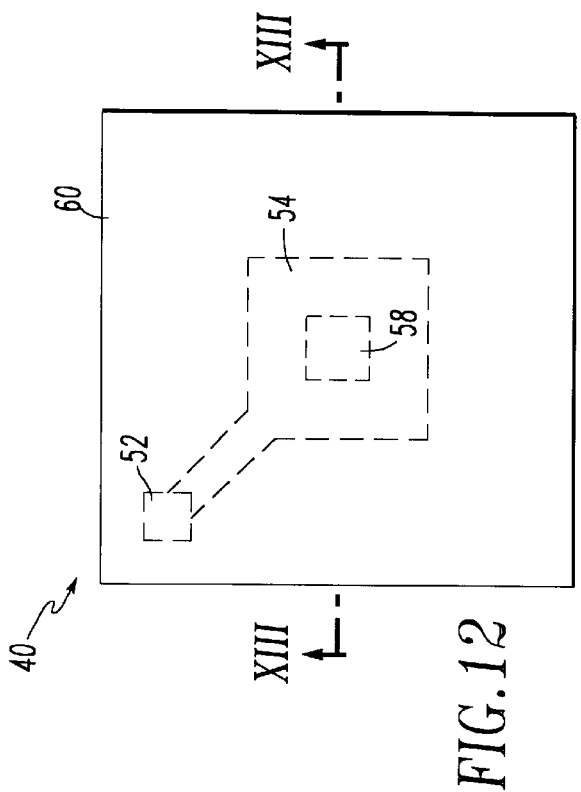
FIG. 12 is a top plan of the substrate assembly of FIG. 10 after etching of the substrate.
Figure 13:
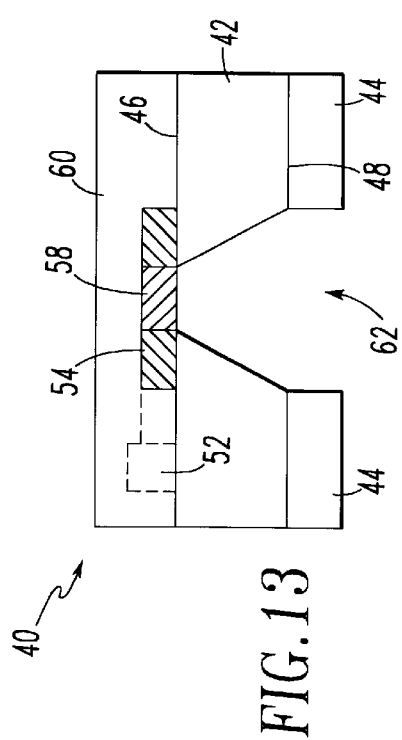
FIG. 13 is a cross-sectional side-view of the substrate assembly of FIG. 12.

FIGS. 12 and 13 illustrate the substrate assembly 40 after a portion of the substrate 42 has been removed defining a cavity 62. The cavity 62 may be formed, for example, by anisotropic bulk etching of the substrate 42. Only that portion of the substrate 42 exposed by the etching mask 44 is removed. The cavity 62 extends from the second surface 48 to the first surface 46, exposing the sensing electrode 58. Performing the bulk etching of the substrate 42 prior to patterning the diffusion barrier 60 permits the diffusion barrier 60 to act as a mask for the first surface 46 of the substrate 42.

Figure 14:
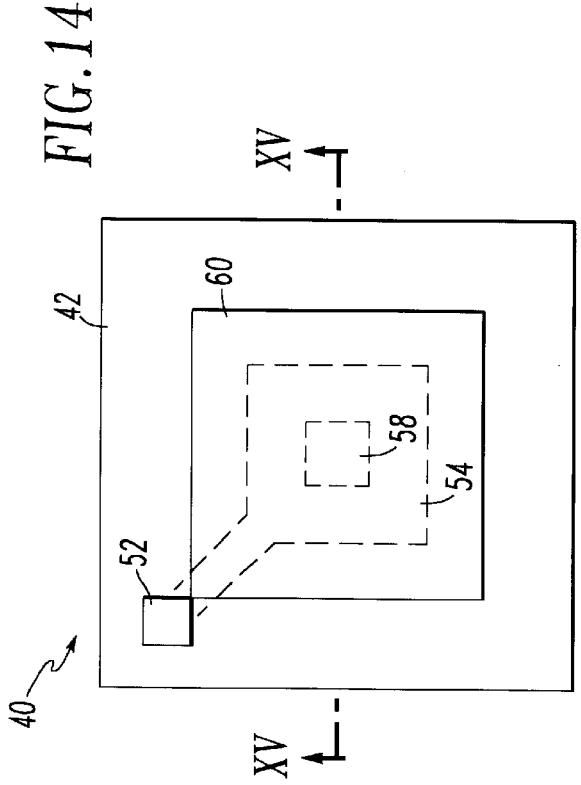
FIG. 14 is a top plan view of the substrate assembly of FIG. 12 after patterning of the diffusion barrier.
Figure 15:
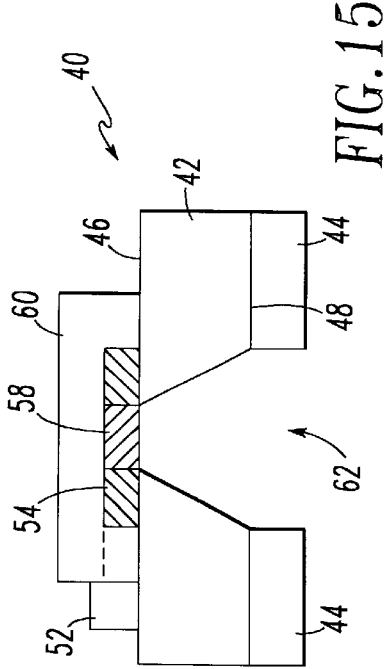
FIG. 15 is a cross-sectional side-view of the substrate assembly of FIG. 16.

FIGS. 14 and 15 illustrate the substrate assembly 40 after patterning of the diffusion barrier 60. The diffusion barrier 60 is patterned, such as by conventional surface etching techniques, to expose the contact pad 52. However, the diffusion barrier 60 remains in contact with the sensing electrode 58, the sensing electrode lead 54, and the substrate 42 after patterning. Because MEMS fabrication techniques allow the thickness of the diffusion barrier 60 to be on the order of one micron, as described hereinbefore, the response time of the sensor with the substrate assembly 40 having the sensing electrode 58 and the diffusion barrier 60 formed thereon may be less than one hundred ms. Moreover, using MEMS fabrication techniques allows the final assembly of the sensor to be much smaller than conventional electrochemical gas sensors, having a volume of approximately 10 cubic millimeters.

Figure 16:
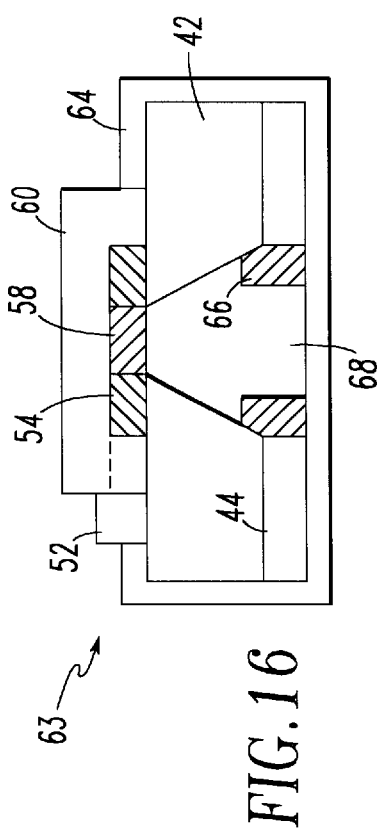
FIG. 16 is a cross-sectional side-view of the electrochemical gas sensor according to the present invention.

FIG. 16 illustrates a cross-sectional side-view of an electrochemical gas sensor 63 according to the present invention having the substrate assembly 40. The gas sensor 63 includes a housing 64, a counter electrode 66, and an electrolyte 68 added to the substrate assembly 40. The housing 64 protects the substrate assembly 40 and may be constructed of an electrically insulating material such as, for example, plastic or ceramic. The etching mask 44 may remain on the substrate assembly 40, as illustrated in FIG. 16, or it may be removed. The counter electrode 66 is an electrically conductive material such as, for example, lead. The counter electrode 66 may be connected to the housing 64 and the substrate assembly 40.

Figure 17:
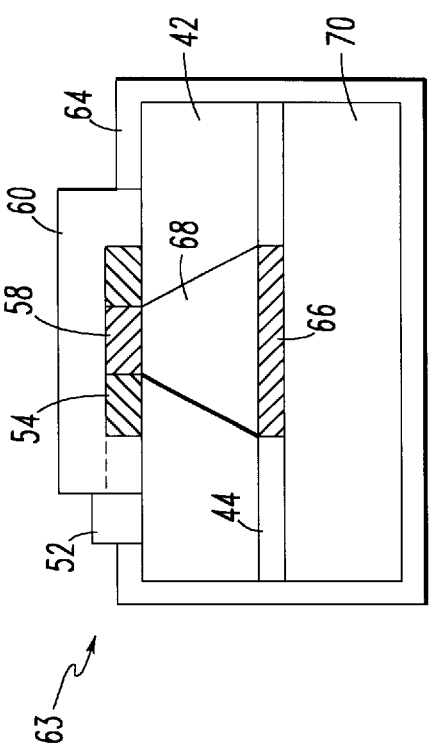
FIG. 17 is a cross-sectional view of an electrochemical gas sensor according to another embodiment of the present invention.

In an alternative embodiment, illustrated in FIG. 17, the counter electrode 66 is formed on a second substrate assembly 70 using, for example, MEMS fabrication techniques, as described hereinbefore. According to this embodiment, the second substrate assembly 70 is then bonded to the substrate assembly 40 using, for example, conventional wafer bonding techniques.

The electrolyte 68 may be, for example, an aqueous solution of potassium hydroxide. The electrolyte 68 fills the cavity 62 in the substrate 42, thereby forming an electrochemical cell between the sensing electrode 58 and the counter electrode 66.

Figure 18:
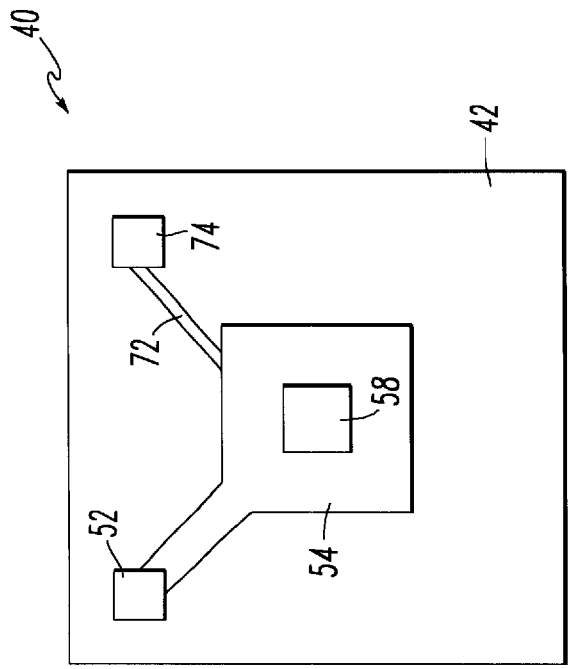
FIG. 18 is a top plan view of a substrate assembly at a stage in the process of manufacturing an electrochemical gas sensor according to another embodiment of the present invention.

With the sensing electrode 58 and diffusion barrier 60 formed on the substrate assembly 40, the electrochemical gas sensor 63 of the present invention allows for the integration of other sensing elements and electronic circuits. For example, FIG. 18 is a top plan view of the substrate assembly 40 having an integrated resistance temperature detector (RTD) as a second sensing element formed on the substrate assembly 40. To integrate the RTD, before deposition of the diffusion barrier 60, a thin film 72 of metal, such as platinum, is deposited on the first surface 46 of the substrate 42 adjacent the sensing electrode lead 54. The thin film 72 may be, for example, laser trimmed to a desired aspect ratio to form the RTD. A second contact pad 74 in electrical contact with the thin film 72 may be formed on the substrate 42 in the same or similar fashion that the contact pad 52 was formed. The second contact pad 74 permits the resistant measurement for the monitoring of temperature in the environment of the sensing electrode 58. According to this embodiment, it is possible to do an in-situ temperature compensation of the sensor output, which may be desirous in certain applications, such as oxygen monitoring in an air-way of a ventilator.

Figure 19:
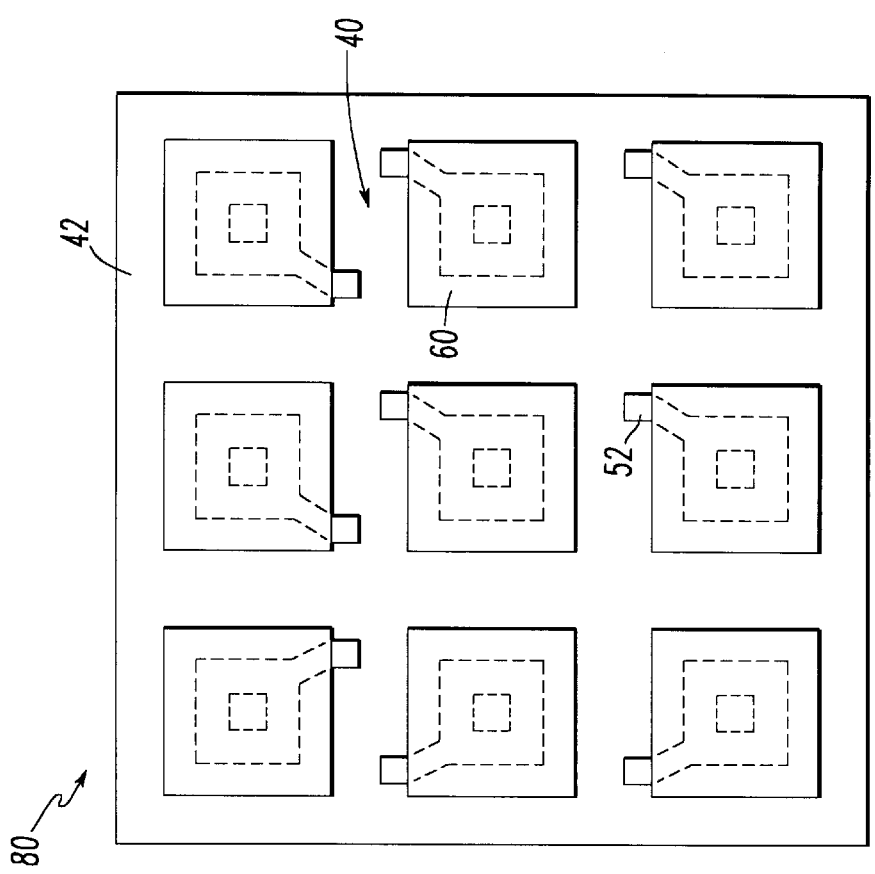
FIG. 19 is a top plan view of an electrochemical gas sensor array according to the present invention.

The RTD structure illustrated in FIG. 18 is but one example of a component which may be integrated with the sensor 63 according to the present invention. Any electrical circuit capable of being formed on the substrate assembly 40, such as, for example, compensating electrical circuits, may be integrated with the sensor 63. In addition, other gas sensors may be integrated on the substrate. Thus, sensors which detect separate gases may be formed on a single substrate 42 to form a gas sensor array 80, as illustrated in FIG. 19, which illustrates the array 80 at one stage in the process of manufacturing the array 80. The embodiment illustrated in FIG. 19 depicts the substrate assemblies 40 for an array 80 of nine sensors, although in other embodiments a different number of sensors may be formed on the substrate 42. In order for the various sensors comprising the array 80 to detect different gases, different electrolytes such as, for example, sulfuric acid and phosphoric acid, may be used. Different materials for forming the sensing electrodes 58 and the diffusion barriers 60 need not be used, however, to create sensors which detect different gases, thus simplifying the process of manufacturing the array 80. In addition, an array 80 of sensors built on the MEMS level are much smaller than conventional relevant art gas sensor arrays because of the reduced scale of MEMS devices in comparison to their macroscale counterparts.

Figure 20:
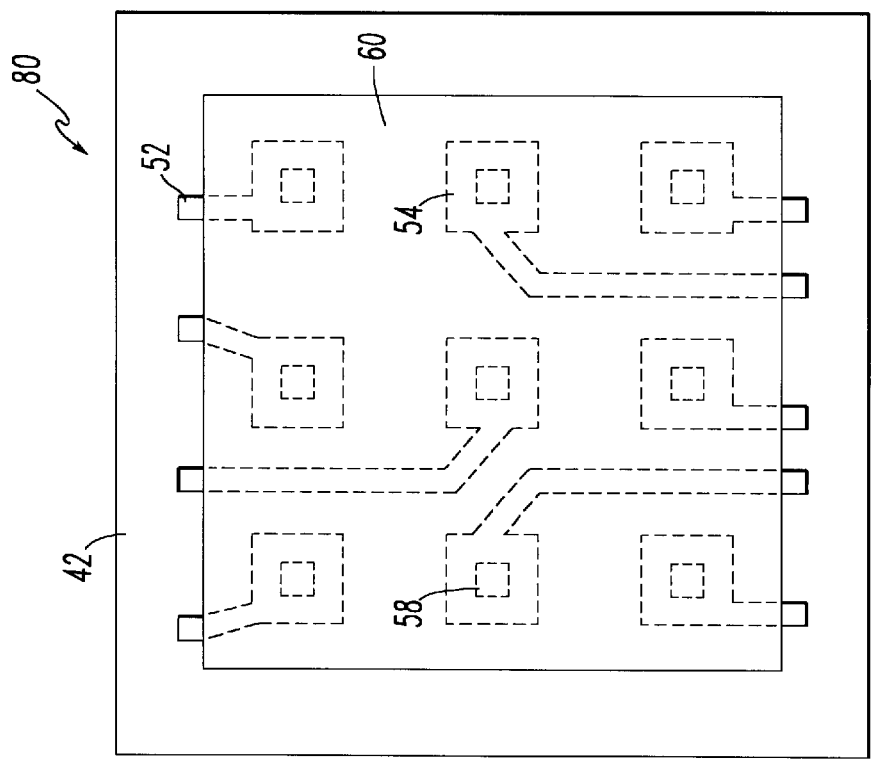
FIG. 20 is a top plan view of an electrochemical gas sensor array according to another embodiment of the present invention.

FIG. 20 illustrates another embodiment of an electrochemical gas sensor array 80 according to the present invention. According to the embodiment illustrated in FIG. 20, one diffusion barrier 60 is in contact with the sensing electrodes 58. The diffusion barrier 60 is patterned to expose the contact pads 52.

Those of ordinary skill in the art will recognize that many modifications and variations of the present invention may be implemented. The foregoing description and the following claims are intended to cover all such modifications and variations. Furthermore, the materials and processes disclosed are illustrative, but are not exhaustive. Other materials and processes may also be used to make devices embodying the present invention. Moreover, the present invention may be realized by performing the steps in processes described herein in various sequences.

What is claimed is:

1. An electrochemical gas sensor, comprising:
   a substrate defining an opening therethrough;
   a sensing electrode connected to a first surface of the substrate and adjacent a first end of the opening;
   a diffusion barrier connected to the sensing electrode;
   a counter electrode adjacent a second end of the opening;
   an electrolyte located in the opening between the sensing electrode and the counter electrode; and
   a housing encapsulating the substrate, the counter electrode, and the electrolyte.

2. The sensor of claim 1, wherein the sensing electrode includes a noble metal selected from the group consisting of gold, silver, platinum, and rhodium.

3. The sensor of claim 1, wherein the diffusion barrier includes a first portion connected to the sensing electrode and a second portion connected to the first surface of the substrate.

4. The sensor of claim 1, further comprising a sensing electrode lead connected to the sensing electrode.

5. The sensor of claim 4, wherein the sensing electrode lead is connected to the first surface of the substrate.

6. The sensor of claim 4, wherein the sensing electrode lead includes a noble metal selected from the group consisting of gold, silver, platinum, and rhodium.

7. The sensor of claim 4, further comprising a contact pad connected to the sensing electrode lead.

8. The sensor of claim 7, wherein the contact pad includes a metal selected from the group consisting of gold and aluminum.

9. The sensor of claim 7, further comprising a second sensing element connected to the first surface of the substrate.

10. The sensor of claim 9, wherein the second sensing element includes a metallic film connected to the first surface of the substrate.

11. The sensor of claim 10, wherein the metallic film includes platinum.

12. The sensor of claim 9, further comprising a second contact pad connected to the second sensing element.

13. An electrochemical gas sensor, comprising:
    a substrate defining an opening therethrough;
    a sensing electrode connected to a first surface of the substrate and adjacent a first end of the opening;
    a diffusion barrier connected to the sensing electrode;
    a counter electrode adjacent a second end of the opening;
    an electrolyte located in the opening between the sensing electrode and the counter electrode; and
    a sensing electrode lead connected to the sensing electrode, and wherein the sensing electrode lead is connected to the first surface of the substrate.

14. The sensor of claim 13, wherein the sensing electrode lead includes a noble metal selected from the group consisting of gold, silver, platinum, and rhodium.

15. The sensor of claim 13, further comprising a contact pad connected to the sensing electrode lead.

16. The sensor of claim 15, wherein the contact pad includes a metal selected from the group consisting of gold and aluminum.

17. The sensor of claim 13, further comprising a second sensing element connected to the first surface of the substrate.

18. The sensor of claim 17, wherein the second sensing element includes a metallic film connected to the first surface of the substrate.

19. The sensor of claim 18, wherein the metallic film includes platinum.

20. The sensor of claim 17, further comprising a second contact pad connected to the second sensing element.

21. An electrochemical gas sensor, comprising:
    a substrate defining an opening therethrough;
    a sensing electrode connected to a first surface of the substrate and adjacent a first end of the opening;
    a diffusion barrier connected to the sensing electrode;
    a counter electrode adjacent a second end of the opening;
    an electrolyte located in the opening between the sensing electrode and the counter electrode;
    a sensing electrode lead connected to the sensing electrode; and
    a contact pad connected to the sensing electrode lead.

22. The sensor of claim 21, wherein the contact pad includes a metal selected from the group consisting of gold and aluminum.

23. The sensor of claim 21, further comprising a second sensing element connected to the first surface of the substrate.

24. The sensor of claim 23, wherein the second sensing element includes a metallic film connected to the first surface of the substrate.

25. The sensor of claim 24, wherein the metallic film includes platinum.

26. The sensor of claim 23, further comprising a second contact pad connected to the second sensing element.

27. An electrochemical gas sensor array, comprising:
    a substrate defining a plurality of openings therethrough, each opening having a first end and a second end;
    a plurality of sensing electrodes connected to a first surface of the substrate, each adjacent the first end of one of the openings;
    at least one diffusion barrier connected to at least one of the sensing electrodes;
    a plurality of counter electrodes, each adjacent the second end of one of the openings; and
    a plurality of electrolytes, each located in one of the openings between one of the sensing electrodes and one of the counter electrodes.

28. The sensor array of claim 27, wherein the plurality of electrolytes are selected from the group consisting of potassium hydroxide, sulfuric acid, and phosphoric acid.

29. The sensor array of claim 27, wherein the at least one diffusion barrier is one of a plurality of diffusion barriers, wherein each of the diffusion barriers is connected to one of the sensing electrodes.

30. The sensor array of claim 27, further comprising a plurality of sensing electrode leads, each sensing electrode lead connected to one of the sensing electrodes.

31. The sensor array of claim 30, further comprising a plurality of contact pads, each connected to one of the sensing electrode leads.

* * * * *